US006592897B1

(12) United States Patent
Bengs et al.

(10) Patent No.: US 6,592,897 B1
(45) Date of Patent: Jul. 15, 2003

(54) SLOW RELEASE TABLET PREPARED FROM LINEAR WATER-INSOLUBLE POLYSACCHRIDES

(75) Inventors: Holger Bengs, Frankfurt am Main (DE); Silke Schuth, Ruppach-Goldhausen (DE); Jürgen Grande, Bad Soden (DE); Gitte Böhm, Frankfurt am Main (DE); Arnold Schneller, Messel (DE)

(73) Assignee: Axiva GmbH, Frankfurt am Main (DE)

( * ) Notice: Subject to any disclaimer, the term of this patent is extended or adjusted under 35 U.S.C. 154(b) by 0 days.

(21) Appl. No.: 09/673,072

(22) PCT Filed: Apr. 8, 1999

(86) PCT No.: PCT/EP99/02386
§ 371 (c)(1),
(2), (4) Date: Jan. 25, 2001

(87) PCT Pub. No.: WO99/52558
PCT Pub. Date: Oct. 21, 1999

(30) Foreign Application Priority Data

Apr. 9, 1998 (DE) .......................... 198 16 070

(51) Int. Cl.[7] .............................. A61K 9/22; A61K 9/26
(52) U.S. Cl. ...................................... 424/468; 424/469
(58) Field of Search ................................ 424/468, 469, 424/470, 489, 464, 465

(56) References Cited

FOREIGN PATENT DOCUMENTS

| WO | WO 94/06416 | 3/1994 |
| WO | WO 96/41617 | 12/1996 |
| WO | WO 99/11695 | 3/1999 |
| ZA | 987786 | 8/1998 |

OTHER PUBLICATIONS

"Directly Compressed Tablets Containing Water–Insoluble Glucan and Microcrystalline Cellulose in Addition to Lactose", Masumoto et al., Chem. Pharm. Bull. 31(1), pp. 209–213, (1983).

"Sustained–Release Dosage Forms Containing Chlorpheniramine Maleate with Water–Insoluble Glucan", Masumoto et al., Chem. Pharm. Bull. 32(3), pp. 1055–1062, (1984).

"In Vitro Dissolution Profile in Vivo Absorption Study of Sustained–Release Tablets Containing Chlorpheniramine Maleate with Water–Insoluble Glucan", Masumoto et al., Chem. Pharm. Bull. 32(9), pp. 3720–3723, (1984).

International Search Report for PCT/EP99/02386 dated Sep. 10, 1999.

International Preliminary Examination Report for PCT/EP99/02386 dated Jul. 13, 2000.

*Primary Examiner*—James M. Spear
(74) *Attorney, Agent, or Firm*—Marshall, Gerstein & Borun (57) ABSTRACT

The invention relates to a controlled release tablet which in part or as a whole contains water-insoluble linear polysaccharides, preferably the polysaccharide poly(1,4-α-D-glucan), in the form of microparticles, as retardation material. The tablet is also capable of controllably releasing an active agent.

9 Claims, 5 Drawing Sheets

SLOW RELEASE TABLET PREPARED FROM LINEAR WATER-INSOLUBLE POLYSACCHRIDES

This is the U.S. national phase of International Application No. PCT/EP99/02386 filed Apr. 8, 1999, the entire disclosure of which is incorporated herein by reference.

BACKGROUND OF THE INVENTION

1. Field of the Invention

The present invention relates to slow-release tablets comprising linear water-insoluble polysaccharides, a process for preparation, and use thereof, in particular for the controlled release of active compounds.

2. Description of Related Technology

In modern pharmaceutical technology, formulations of excipients whose administration form specifically brings an influence to bear on the biodistribution, bioavailability, biocompatibility and absorption are of importance. Moreover, excipients must have good mechanical properties, such as adequate hardness and resistance to tension and stress. Although a few compounds can already be pressed themselves to give compact stable masses (e.g. sucrose or lactose), ingredients—tablet auxiliaries—are also necessary, such as binders, fillers, lubricants and additives. Typical dry binders for increasing stability which are used here are:

calcium phosphates, microcrystalline cellulose (e.g. Avicel®, PH 102®, especially Celsphere), polyvinylpyrrolidones (e.g. Kollidon®, Luviskol VA 64®, Plasdone®), corn, wheat or potato starch, derivatized polysaccharides, so-called gums, (e.g. xanthan gum), cellulose derivatives (e.g. hydroxypropylmethylcellulose: Klucel®) or ethylcellulose (Aqualon®). Moreover, the excipients must disintegrate in the body in an optimum and controlled manner in contact with body fluids. Therefore, so-called disintegrants are often added for disintegration control. Typical compounds for this purpose are corn starch, gelatinized starch and starch modifications. Substances which can also be employed are those which develop a disintegrating power due to water absorption and accompanying swelling. These include crosslinked polyvinylpyrrolidones (Kollidon CL®), carboxymethylcellulose and their calcium salts or galactomannans. With some compounds (e.g. Avicel® and PH 102®), it is possible to achieve both the necessary mechanical stability and to control tablet disintegration.

Specific starches, including amylose, are described as advantageous excipients for tablet formulation (Journal of Pharmaceutical Sciences 55 (1966), 340). However, the Nepol amylose used (A. E. Stanley Manufacturing Co., USA) proves disadvantageous, since the active compounds are not exhaustively released and the excipient has a high water content (10–12%), which is why hydrolytically labile active compounds cannot be formulated. In particular, crosslinked amylose (degree of crosslinkage 15%) is as a superior binding agent described (S.T.P. Pharma Sciences 4 (1994), 329–335 and Journal of Controlled Release 15, (1991) 39–46, Journal of Controlled Release 15, (1991) 3946), which on account of its water absorption capacity acts as a disintegration accelerator. In WO 94/21236, crosslinked amylose (degree of crosslinkage 25%) is used as a binder and disintegrant. A high degree of crosslinkage, however, has a disadvantageous effect on the biological compatibility. The crosslinking agent used is up to 30% by weight of the intolerable epichlorohydrin. Even low crosslinkages in the range of a few percent lead to a rapidly growing slowness to react, so residues of unreacted crosslinker which remain have to be expected.

All starch- and amylose-containing excipients on the market until now use plant sources of origin.

It is disadvantageous here that these biopolymers, like all naturally occurring substances, have considerable variations in composition and structure and therefore the necessary reproducibility and thus constant product quality is not guaranteed, even with respect to controlled release of active compound.

In the case of native starch, the content of amylose and amylopectin varies considerably depending on the origin. For example, starch from potatoes contains about 20% by weight of amylose and about 80% by weight of amylopectin, whereas starch from corn contains about 50% by weight of amylose and about 50% by weight of amylopectin. Additional variance within a plant community results due to soil condition, fertilizer absorption, seasonal climatic differences etc.

Moreover, amylose, a 1,4-linked polyglucan, having a molecular weight of approximately 50,000 to 150,000 daltons, and amylopectin, a highly branched 1,4- and 1,6-linked polyglucan, having a molecular weight of approximately 300,000 to 2,000,000 daltons, have wide molecular weight distributions.

The transitions from highly branched to linear are fluid and vary in the original plant material, so that a sharp delimitation is almost impossible. In particular, excipients which still contain amylopectin cause irregular swelling on account of the branchings, whereby the carrier stability is adversely affected. Amylopectin is therefore usually laboriously removed by means of enzymatic debranching (Journal of Controlled Release 45, (1997) 25–33 and EP 0499 648 B1=U.S. Pat. No. 5,468,286).

Beside these marked disadvantages, the wide molecular weight distribution or mixtures of polymers of different spatial arrangements, native polymers contain further constituents such as low molecular weight compounds, e.g. fats and oils, which can only be separated with difficulty and have a disadvantageous effect in further processing and application (e.g. U.S. Pat. No. 3,490,742). In particular, yield-decreasing working steps have to be carried out, in some cases it not being possible to eliminate impurities completely.

Experiments are also known to optimize biopolymers, i.e. even starch, by genetically modifying the plant of origin. WO 94/03049 describes the preparation and use of high amylose-containing starch from genetically modified corn. Regardless thereof, the disadvantages of nonuniformity and contamination remain.

The reproducibility and quality is substantially dependent on the uniformity and purity. To guarantee products of high quality, these starting substances must be clearly definable and characterizable.

SUMMARY OF THE INVENTION

The present invention has the object, while avoiding the above disadvantages, of making available a slow-release material which can be used as a slow-release tablet in a pharmaceutical composition for the controlled release of active compounds, preferably for oral administration.

The object is achieved by using as the slow-release material water-insoluble linear polysaccharides which are biocompatible, chemically inert, pressure-stable starting materials which make possible the controlled release of active compound without further additives. Preferably, the starting material used is linear water-insoluble poly(1,4-alpha-D-glucan) as such or in the form of spherical microparticles.

DETAILED DESCRIPTION OF THE INVENTION

"Slow-release tablets" in the sense of the present invention are, in particular, tablets, coated tablets, pills, pellets, pressings, small plates, disks and the like, whose formulation requires compression. Likewise to be included are capsules which are filled with the slow-release material.

Slow-release materials are to be regarded in the following as linear water-insoluble polysaccharides.

Linear water-insoluble polysaccharides in the sense of the present invention are polysaccharides, preferably polyglucans, in particular poly(1,4-alpha-D-glucan), which consist of monosaccharides, disaccharides, further oligomers thereof or derivatives.

These are always linked to one another in the same way. Each base unit defined in this way has exactly two linkages, each one to another monomer. Excluded therefrom are the two base units, which form the beginning and end of the polysaccharide. These base units have only one linkage to a further monomer. In the case of three or four linkages (covalent bonds) of a monomer to another group, preferably a further saccharide unit, branching is referred to. At least three glycosidic bonds then leave from each saccharide unit in the polymer backbone.

According to the invention, branchings do not occur or only occur to such an insignificant extent that, in the very small branching proportions present, in general they are no longer accessible to the conventional analytical methods. This is the case, for example, when based on the totality of all hydroxyl groups present to one hundred hydroxyl groups which are not needed for the synthesis of the linear polysaccharide, at most five hydroxyl groups are taken by linkages to other saccharide units.

The degree of branching here is maximal (100%) if, on each saccharide unit, the free hydroxyl groups (or other functional groups occurring) have further glycosidic (or other) bonds to further saccharides. The degree of branching is minimal (0%) if, in the saccharides, apart from the hydroxyl groups which determine the linearity of the polymer, no further hydroxyl groups are modified by chemical reaction.

Examples of preferred water-insoluble linear polysaccharides are linear poly-D-glucans, where the type of linkage is insignificant as long as linearity in the sense of the invention is present. Examples are poly(1,4-alpha-D-glucan) and poly(1,3-beta-D-glucan), poly(1,4-alpha-D-glucan) being particularly preferred.

If the base unit has three or more linkages, this is referred to as branching. The so-called degree of branching results here from the number of hydroxyl groups per 100 base units which are not involved in the synthesis of the linear polymer backbone and which form branchings.

According to the invention, the linear water-insoluble polysaccharides have a degree of branching of less than 8%, i.e. they have less than 8 branchings to 100 base units. Preferably, the degree of branching is less than 4% and in particular at most 1.5%.

If the water-insoluble linear polysaccharide is a polyglucan, e.g. poly(1,4-alpha-D-glucan), the degree of branching in the 6-position is less than 4%, preferably at most 2% and in particular at most 0.5%, and the degree of branching in the other positions not involved in the linear linkage, e.g. the 2- or 3-position in the case of the preferred poly(1,4-alpha-D-glucan), is preferably in each case at most 2% and in particular at most 1%. Particularly preferred are polysaccharides, in particular poly-alpha-D-glucans, which have no branchings, or whose degree of branching is so minimal that it is no longer detectable using conventional methods.

According to the invention, the prefixes "alpha", "beta" or "D" on their own relate to the linkages which form the polymer backbone and not to the branchings.

"water insolubility" in the sense of the present invention means that no detectable solubility of the compound exists under normal conditions (room temperature of 25° C. and an air pressure of 101325 pascals or based on values differing at most 20% therefrom).

In the case of the polysaccharides used according to the invention, in particular of the polyglucans such as poly(1,4-alpha-D-glucan), this means that at least 98% of the amount employed, preferably an amount of greater than 99.5%, is insoluble in water. The term insolubility here can also be explained with the aid of the following observation. If 1 g of the linear polysaccharide to be investigated is heated to 130° C. in 1 I of deionized water under a pressure of 1 bar, the resulting solution only remains stable briefly, for a few minutes. On cooling under normal conditions, the substance reprecipitates. After a further cooling and separation using the centrifuge with inclusion of experimental losses, at least 66% of the amount employed can be recovered in this way.

In the context of this invention, linear, water-insoluble polysaccharides are preferably used which can be obtained with the aid of generally defined biotechnological or genetic engineering methods. A particularly advantageous embodiment of the invention described here is the preparation in a biotechnological process, in particular in a biocatalytic process.

Linear polysaccharides prepared by biocatalysis (also: biotransformation) in the context of this invention means that the linear polysaccharide is prepared by catalytic reaction of monomeric base units such as oligomeric saccharides, e.g. of mono- and/or disaccharides, by using a so-called biocatalyst, customarily an enzyme, under suitable conditions. Preferably, poly(1,4-alpha-D-glucan) in particular is prepared by means of polysaccharide syntheses and/or starch syntheses and/or glycosyl transferases and/or alpha-1,4-glucan transferases and/or glycogen synthases and/or amylosucrases and/or phosphorylases.

Likewise conceivable are linear polysaccharides from fermentation. In the context of this invention, these are linear polysaccharides which can be obtained by enzymatic processes using naturally occurring organisms, such as fungi, algae or microorganisms or using organisms not occurring naturally, which can be obtained by modification of natural organisms, such as fungi, algae or microorganisms, by means of generally defined genetic engineering methods.

Moreover, linear polysaccharides can be obtained for the preparation of the slow-release tablet described in the present invention from nonlinear polysaccharides which contain branchings by treating them with an enzyme and linear polymers thereof can be obtained with cleavage (e.g. by means of enzymes, such as amylase, isoamylase, gluconohydrolase, pullulanase, inter alia) and removal of the branchings.

The molecular weights $M_w$ of the linear polysaccharides used according to the invention can vary in a wide range from $10^3$ g/mol to $10^7$ g/mol, the molecular weights $M_w$ preferably lie in the range from $2 \times 10^3$ g/mol to $5 \times 10^4$ g/mol, in particular $3 \times 10^3$ g/mol to $2 \times 10^4$ g/mol. For the linear polysaccharide poly(1,4-alpha-D-glucan) preferably used, corresponding ranges are used.

The molecular weight distribution or polydispersity $M_w/M_n$ can vary within wide ranges depending on the method of preparation of the polysaccharide. A polydispersity of 1.01 to 50 is preferably employed, particularly preferably from 1.5 to 15. In this case, the polydispersity increases with a bimodal distribution of the molecular weights, this not adversely affecting the properties of the tablet formulation.

Mixtures of linear polysaccharides according to the invention and in the form of microparticles with nonlinear polysaccharides are not excluded. "Controlled release of active compound" is understood as meaning that the active compound is released after a certain time and/or period of time in a dose advantageous for the biological organism with acceptance of a statistical deviation corresponding to the circumstances.

This definition also includes extremes. On the one hand, the spontaneous release of all active compounds present in the formulation within a period of time approximating to the value zero, on the other hand, the minimal necessary amount dose for the attainment of a therapeutic effect over a long, even infinite period of time, at least a period of time which is necessary to release all active compounds present in the formulation.

For the slow-release formulation present here, therefore, reference is synonymously made to a depot formulation or formulation having delayed release. An "active compound" is regarded as any biologically active substance and substance combination in the widest sense (specifically in the human and veterinary area), in particular for medicinal indication. In particular: analgesics, anginal preparations, antiallergics, antihistamines, antiinflammatories, bronchodilators, bronchospasmolytics, diuretics, anticholinergics, antiadhesion molecules, cytokine modulators, biologically active endonucleases, recombinant human DNases, neurotransmitters, leukotriene inhibitors, vasoactive intestinal peptides, endothelin antagonists, analeptics, local anesthetics, anesthetics, antiepileptics, anticonvulsants, antiparkinson agents, antiemetics, compounds regulating or stimulating the hormone system, compounds regulating or stimulating the cardiovascular system, compounds regulating or stimulating the respiratory tract system, vitamins, trace elements, antioxidants, cytostatics, antimetabolites, antiinfectives, immunomodulators, immunosuppressants, antibiotics, proteins, peptides, hormones, growth hormones, growth factors, xanthines, vaccines, steroids and beta$_2$-mimetics.

"Therapeutic effect" in the sense of this invention means that a therapeutically effective amount of an active compound reaches the desired target site, displays its action there, and causes a physiological reaction. The palliative and/or curative effect is included.

"Biocompatible" in the sense of this invention means that the polysaccharides employed are subjected to complete biodegradation and no concentration in the body takes place. Biodegradation here is understood as meaning any process taking place in vivo which leads to a degradation or destruction of the polymer. In particular, hydrolytic or enzymatic processes are likewise included in this area. For the biocompatibility of the polysaccharides and of its degradation products (metabolites), not least is the naturally identical character of the polysaccharides employed of high importance. Therefore, the polysaccharides used according to the invention are suitable for therapeutic, diagnostic or prophylactic use. The term "pharmaceutically acceptable" in the sense of this invention means that a vehicle for an active compound, an auxiliary or alternatively so-called excipient, can be absorbed by a living being without significant side effects arising for the organism.

The tablets are prepared by mixing the starting components, the linear polysaccharide being mixed or homogenized together with the active compound according to known methods, e.g. with the aid of a ball mill. The active compound can have a concentration of up to 50%, a concentration between 1 and 20%, particularly preferably between 5 and 15%, preferably being used. Further customary auxiliaries and additives can be employed. The sum of active compound and polysaccharide according to the invention in the total composition (including possible auxiliaries and additives) should be at least 50%, however 70 to 100% is preferred and 85 to 98% is particularly preferred. The composition of the auxiliaries can vary within wide ranges, the ratios of the composition depending on the interactions with the active compound and the linear water-insoluble polysaccharide.

Auxiliaries which can be employed in tablet production and in the preinserted mixing process are solvents, readily volatile solvents being preferred.

The parent structure of the polysaccharide according to the invention for tablet production can be an amorphous or crystalline structure or grain, such as is obtained directly in synthesis, or alternatively a microparticle, such as is described by the patent application (German Patent Office, ref.: 197 37 481.6). The simple mixing process is preferably used for the preparation of the raw material or raw mixture of the tablet. This preparation procedure of the tablets can affect the properties of the tablet. For example, it is possible to couple the active compound directly on or to the parent structure of the polysaccharide by spraying techniques, for example in the fluidized bed process or by coating in a suspension of the polysaccharide used according to the invention. Absorption processes can be employed here, in which the porous structure of the microparticles is utilized in order to absorb the active compound in a solution (sponge character), or spray-drying techniques. Here, a solution, suspension or emulsion of a linear polysaccharide and of the active compound is dried by means of known spray technologies. In the case of solutions, corresponding organic solvents are employed. Higher temperatures or pressures, and supercritical processes can help to produce the necessary solubilities for short periods of time.

The pressures used during tablet production can vary within wide ranges. Pressure variations can be specifically employed with the polysaccharides described according to the invention to achieve an additionally positively acting slow-release effect. The pressures can vary within wide ranges from 1 MPa to $10^3$ MPa. ($10^5$ Pa=1 bar). Pressures in the range from 10 MPa to 300 MPa are preferably to be employed, particularly advantageously pressures in the range from 100 MPa to 250 MPa.

BRIEF DESCRIPTION OF THE DRAWINGS

The following examples and figures serve for further explanation of the invention, without restricting it to products and embodiments described in the examples.

EXAMPLES

The following examples relate in particular to the preparation of microparticles, as described in the patent application (German Patent Office, ref.: 197 37481.6), to which reference is expressly made. In addition, a particularly advantageous method for the preparation of poly(1,4-alpha-D-glucan) is described in WO 95/31553.

Example 1

In-vitro Production of Poly(1,4-α-D-glucan) in a Biocatalytic Process with the Aid of the Enzyme Amylosucrase 10 l of a 20% strength sucrose solution are added to a sterilized (steam sterilization) 15 l vessel. The enzyme extract comprising amylosucrase obtained by means of fermentation is added to the sucrose solution in one portion. The enzyme activity is 16 units (1 unit corresponds to the reaction of 1 µmol of sucrose per minute per mg of enzyme). The apparatus is provided with a KPG stirrer, which is also sterilized. The vessel is sealed and kept at 40° C. and stirred. After some time, a white precipitate forms. The reaction is ended after a period of time of 180 hours. The precipitate is filtered off and washed a number of times to remove low molecular weight sugars. The residue remaining in the filter is dried at temperatures between 30 and 40° C. in a drying oven with application of a vacuum with the aid of a membrane pump (Vacuubrand GmH & Co, CVC 2). The mass is 685 g (yield 69%).

Example 2

Characterization of the Poly(1,4-α-D-glucan) synthesized with Amylosucrase from Example 1 by Means of Gel Permeation Chromatography 2 mg of the poly(1,4-α-D-glucan) from Example 1 are dissolved in dimethyl sulfoxide (DMSO, p. a. from Riedel-de-Haen) at room temperature and filtered (2 mm filter). One part of the solution is injected into a gel permeation chromatography column. DMSO is used as an eluent. The signal intensity is measured by means of an RI detector and evaluated against pullulan standards (Polymer Standard Systems). The flow rate is 1.0 ml per minute.

The measurement affords a numerical mean of the molecular weight ($M_n$) of 2700 g/mol and a weight mean of the molecular weight ($M_w$) of 11,700 g/mol. This corresponds to a dispersity of 4.3.

Example 3

Preparation of Microparticles of Poly(1,4-α-D-glucan)

400 g of poly(1,4-α-D-glucan) are dissolved in 2 l of dimethyl sulfoxide (DMSO, p.a. from Riedel-de-Haen) at 60° C. in the course of 1.5 h. The solution is then stirred at room temperature for one hour. The solution is added to 20 l of double-distilled water with stirring through a dropping funnel over a period of time of 2 h. The mixture is stored at 6° C. for 40 h. A fine suspension is formed. The particles are separated off by first decanting off the supernatant. The sediment is slurried and centrifuged in small portions (ultracentrifuge RC5C: 5 minutes each at 5000 revolutions per minute). The solid residue is slurried with double-distilled water and centrifuged again a total of three times. The solids are collected and the suspension of about 1000 ml is freeze-dried (Christ Delta 1-24 KD). 283 g of white solid are isolated (Example 3a: yield 71%). The collected supernatants are kept at a temperature of 18° C. overnight. Working up is carried out as described. A further 55 g of white solid are isolated (Example 3b: yield 14%). The total yield is 85%.

Example 4

Desulfurization of the Microparticles from Example 3

To remove dimethyl sulfoxide remaining in the particles, the procedure is as follows. 100 g of the amylose particles from Example 9 are added to 1000 ml of deionized water. The mixture is left by itself for 24 h with slight swirling. The particles are removed as described in Example 9 (ultracentrifuge RC5C: 15 minutes each, 3000 rpm. After freeze-drying, a final weight of 98.3 g results (98% yield). Sulfur determination by elemental analysis gives the following values (test method combustion and IR detection):

sulfur content of the particles from Example 2: 6%+/−0.1% sulfur content of the particles from Example 3: <0.01%

Example 5

Figure 1:
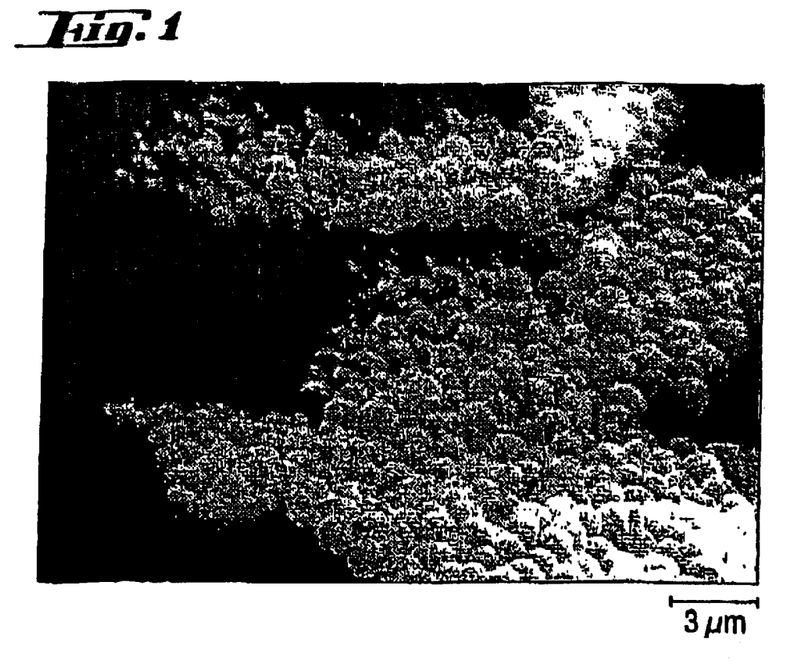
FIGS. 1 and 2 are photographs of poly(1,4-α-D-glucan) microparticles obtained according to the procedure of Example 3.
Figure 2:
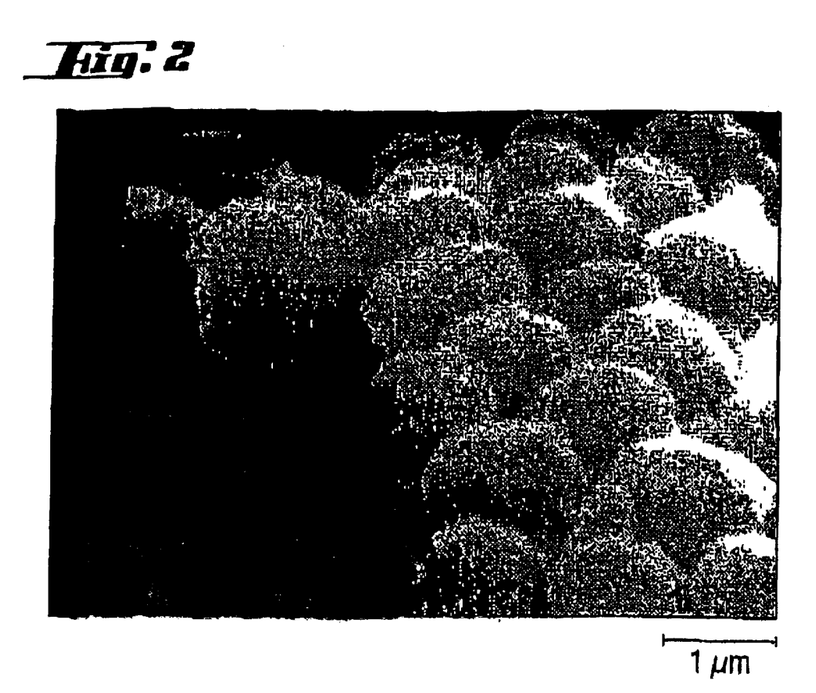

Investigations of the Microparticles from Example 3 by Means of Electron Microscopy To characterize the particles, scanning electron micrographs (SEMs) (Camscan S-4) are carried out. FIGS. 1 and 2 show photographs of the particles which illustrate that they are spherical, very uniform particles with respect to shape, size and surface roughness.

Example 6

Investigations of the Size Distributions of the Particles from Example 3

To characterize the size distributions of the particles from Examples 1 and 9, investigations with a Mastersizer were carried out (Malvem Instruments). The investigation was carried out in the Fraunhofer mode (evaluation: multimodal, number) with a density of 1.080 g/cm$^3$ and volume concentration in the range from 0.012% to 0.014%.

TABLE 1

Characterization of the particle diameters of the microparticles from Example 3

| Example No. | Diameter Dn[*1] (mm) | Dw[*2] (mm) | dw/dn[*3] | Particle distribution d(10%)[*4] (mm) | d(50%)[*5] (mm) | d(90%)[*6] (mm) |
|---|---|---|---|---|---|---|
| 3a | 1.664 | 4.184 | 2.541 | 0.873 | 1.504 | 2.624 |
| 3b | 0.945 | 2.345 | 2.481 | 0.587 | 0.871 | 1.399 |

Dn[*1]: Number average of the diameter
Dw[*2]: Weight average of the diameter
dw/dn[*3]: Dispersity of the particle diameters
d(10%)[*4]: 10% of all particles have a smaller diameter than the value indicated
d(50%)[*5]: 50% of all particles have a smaller diameter than the value indicated
d(90%)[*6]: 90% of all particles have a smaller diameter than the value indicated

Example 7

General Preparation Process of Tablets from Microparticles Comprising Poly(1,4-α-D-glucan)

270 mg of tablet auxiliary (poly(1,4-α-D-glucan)) and 30 mg of active compound are ground in a ball mill (Retsch MM2000) for 10 minutes at an amplitude of 100 (manufacturer's information). 250 mg of the amount homogenized are taken and transferred to a pressing tool (Perkin Elmer, diameter of the ram 13 mm). The pressing tool is placed under a press (Perkin Elmer, hydraulic press). The material is then pressed at a pressure of 2 t for 10 minutes. After releasing the pressure of the apparatus, the finished tablet is carefully removed and stored for further characterization, e.g. stability measurements or release experiments.

In the following, for comparison purposes, tablets are prepared from known tablet formulation materials (comparison examples) such as: microcrystalline cellulose (Avicel™), potato starch (Toffena™-Südstärke), and polyacrylates (Eudragits™-Röhm).

Example 8

Determination of the Active Compound Release as a Function of Time

The release of the tablets prepared according to Example 7 is determined as follows. A tablet is added to 25 ml of water (deionized water) in a 50 ml Erlenmeyer flask. The opening is covered with Parafilm. The flask is fixed to a shaker (IKA Labortechnik; KS 125 basic). The shaker is operated at a setting of about 150 per minute.

After certain times, samples—about 1.5 ml—are removed from the supernatant of the resulting solution. A sufficient amount of this volume is transferred to a disposable cuvette (Sarstedt No. 67.741) and measured in a spectrometer (Kontron Instruments, Uvikon 860). The absorption maxima occurring for the individual active compounds or model substances apply.

Example 9

Absorption Maxima of Further Active Compounds

The absorption maxima of further active compounds were determined as in Example 10. All active compounds mentioned lead to comparable results in the observation of a slow-release effect, as a result of which it is possible to draw conclusions on the variety of possible applications.

TABLE 2

Absorption maxima of various active compounds investigated

| Active compound | Absorption maximum |
|---|---|
| Vitamin $B_{12}$ | 549 nm[*2] |
| Theophylline | 271 nm[*3] |
| Ramorelix ™ | 276 nm[*3] |
| Caffeine | 272 nm[*3] |
| Iloperidone | 274 nm[*3] |
| Buserelin[*1] | 278 nm[*3] |
| Minocycline hydrochloride | 278 nm[*3] |
| Tetracycline hydrate | 269 nm[*3] |
| Phenylephrine | 272 nm[*3] |

[*1]Structure: 5-oxo-L-prolyl-L-histidyl-L-tryptophyl-L-seryl-L-tyrosyl-O-tert-butyl-D-seryl-L-leucyl-L-arginyl-N-ethyl-L-prolinamide
[*2]Disposable cuvette (Sarstedt No. 67.741)
[*3]Quartz cuvette (Hellma, Suprasil ®)

Example 10

Plotting of a Calibration Curve for an Active Compound as Exemplified by the Model Compound Vitamin $B_{12}$ A 1% strength stock solution is prepared by weighing 100 mg of vitamin $B_{12}$ into a 10 ml graduated flask and filling up with deionized water to the calibration mark. By means of a dilution series, concentrations of 0.005%, 0.01% and 0.02% are prepared from this and measured in a spectrometer (Kontron Instruments, Uvikon 860). The extinctions are read off at the absorption maximum of $\lambda$=549 nm. Further measurement points are only necessary if deviations from a straight line are discernible. This calibration straight line serves as a starting point for the determination of the concentration in the supernatant of the active compound release experiment. In the plotting of calibration straight lines of other active compounds and model substances, the data collection is carried out in an analogous manner.

Figure 3:
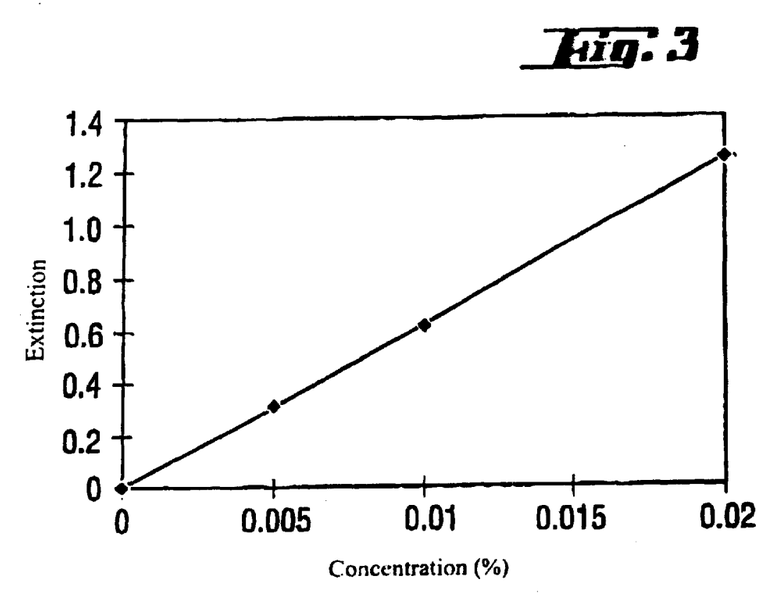
FIG. 3 is a calibration curve for vitamin $B_{12}$ obtained according to Example 10.

The Graphic representation of the calibration for vitamin $B_{12}$ (Extinction in water as a function of the concentration) is shown in FIG. 3.

Example 11

Experiments on the Release of Vitamin $B_{12}$ from Tablets Produced using Poly(1,4-α-D-glucan), and Microparticles Thereof The extinctions of the supernatant of the in-vitro release experiments are measured after specific times, as described in Example 10. In order to go obtain the corresponding concentration values from the calibration curve via the measured extinction, it may be necessary to dilute the supernatants in the ratio 1:10. This factor is accordingly taken into account.

In Table 3, the values are shown in summarized form. In the corresponding FIG. 4, the values are compared in the graph. The maximal possible concentration—according to Example 8 this is 0.1%—was made equal to the value 100% for clearer presentation, so that as a result an estimation is even more possible as to what degree of completeness is achieved after what time.

| Tablet auxiliary | Release (hours) | | | | | | | | | | |
|---|---|---|---|---|---|---|---|---|---|---|---|
| | 0 | 0.5 | 1 | 2 | 3.5 | 6 | 8 | 10 | 24 | 32 | 48 |
| Poly(1,4-α-D-glucan) | 0 | 5.44 | 6.74 | 11.45 | 24.45 | 35.26 | 41.14 | 43.28 | 60.90 | 63.83 | 75.27 |
| Poly(1,4-α-D-glucan) | 0 | 2.23 | 4.87 | 7.57 | 15.32 | 26.11 | 27.20 | 34.78 | 55.02 | 61.21 | 64.30 |
| Poly(1,4-α-D-glucan) | 0 | 4.91 | 5.94 | 8.18 | 19.57 | 30.36 | 36.38 | 36.38 | 67.08 | 74.96 | 87.17 |
| Microparticles of poly(1,4-α-D-glucan) | 0 | 3.97 | 4.03 | 6.52 | 14.22 | 20.37 | 23.71 | 26.12 | 33.23 | 35.70 | 38.18 |
| Microparticles of poly(1,4-α-D-glucan) | 0 | 3.52 | 3.74 | 5.72 | 9.43 | 17.23 | 17.77 | 21.90 | 31.07 | 28.13 | 33.38 |
| Microparticles of poly(1,4-α-D-glucan) | 0 | 3.14 | 3.89 | 5.63 | 11.19 | 18.92 | 22.94 | 22.94 | 39.92 | 46.83 | 53.17 |

Table 3:

Concentration values of the aqueous supernatant as a function of time for the tablet auxiliary materials poly(1,4-α-D-glucan) described according to the invention and microparticles thereof.

Figure 4:
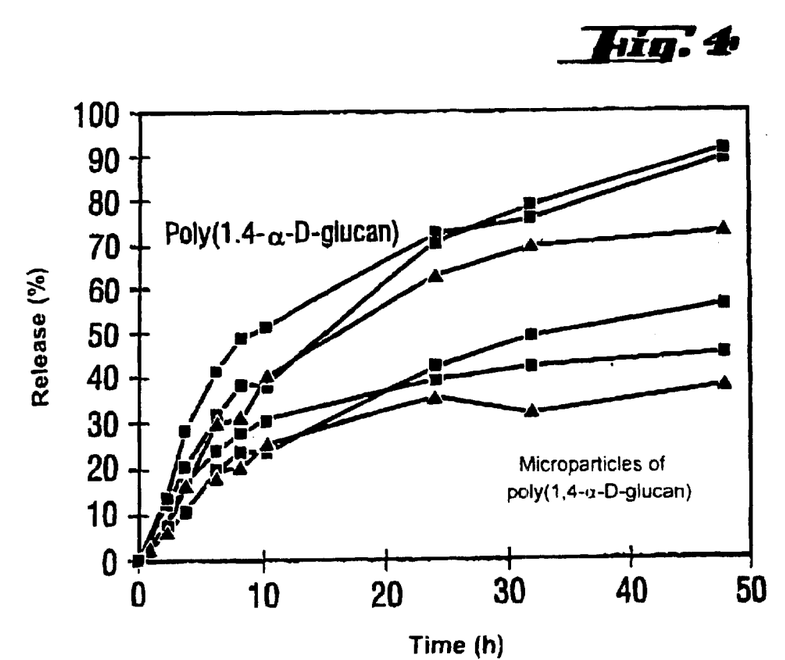
FIG. 4 is a plot of a release of vitamin $B_{12}$ from tablets produced using poly(1,4-α-D-glucan) microparticles obtained according to Example 11.

The release of vitamin $B_{12}$ from tablets of various auxiliaries: a) poly(1,4-α-D-glucan) and b) microparticles of poly(1,4-α-D-glucan) is shown in FIG. 4.

Example 12

Experiments on the Release of Vitamin $B_{12}$ from Tablets Produced using Microcrystalline Cellulose (Avicel™) and Potato Starch (Toffena™) (Comparison Examples)

Figure 5:
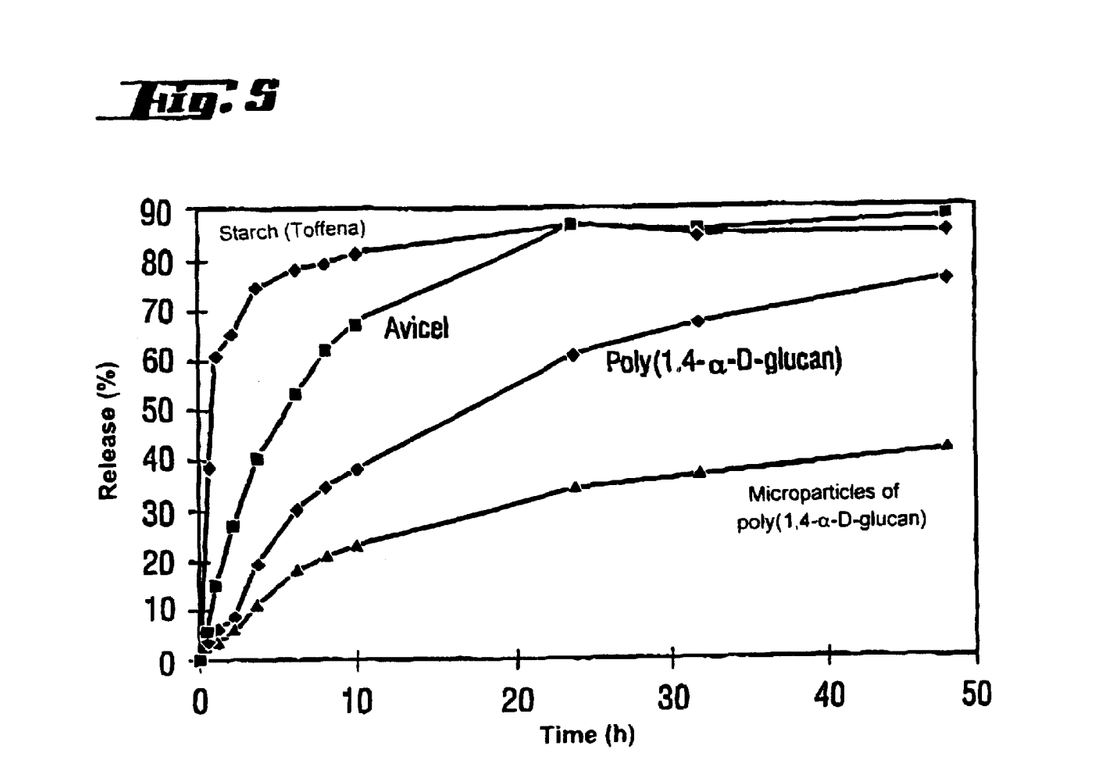
FIG. 5 is a plot illustrating release of vitamin $B_{12}$ from tablets of various auxiliaries according to Example 12.

The results shown in Table 4 were measured and calculated as described in Example 11. FIG. 5 shows in comparative form the results of the tablet auxiliaries poly(1,4-α-D-glucan) and microparticles of poly(1,4-α-D-glucan) described according to the invention to the comparison substances microcrystalline cellulose (Avicel™) and potato starch (Toffena™). The slow-release effect is clearly to be discerned here.

cellulose (Avicel™) (comparison example) and d) potato starch (Toffena™) comparison example. (For clearer representation, the mean values of the values indicated in Tables 3 and 4 were calculated).

Example 13

Experiments on the Release from Theophylline Tablets Consisting of Poly(1,4-α-D-glucan) and Microparticles of Poly(1,4-α-D-glucan)

Figure 6:
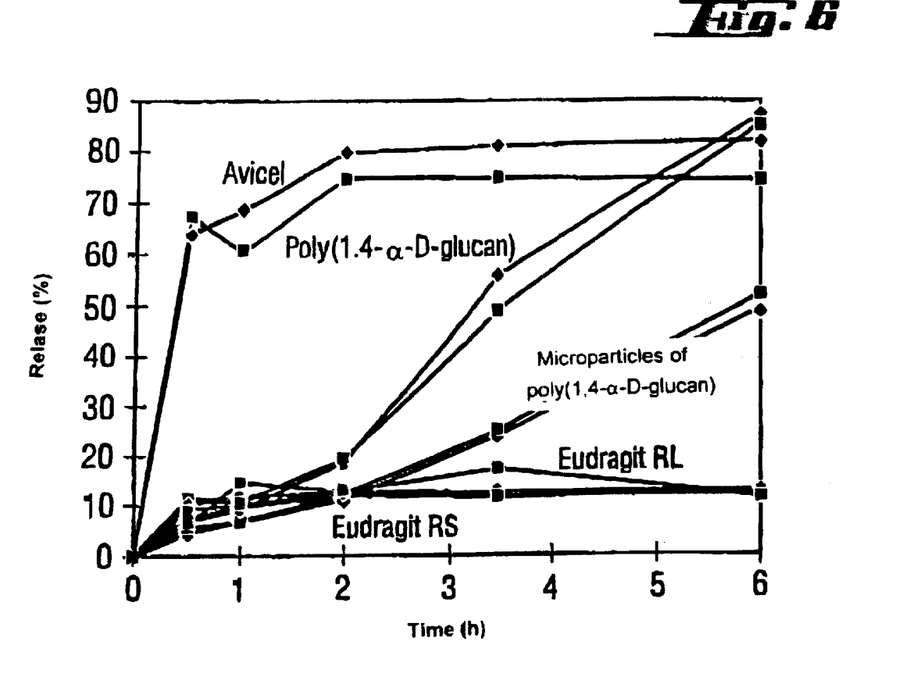
FIG. 6 is a plot showing the release of theophylline from tablets of various auxiliaries according to Example 13 and 14.

The experiments on the release of theophylline from tablets consisting of various tablet auxiliaries are carried out analogously to Example 12. The tablet auxiliary used is poly(1,4-α-D-glucan), which was obtained directly from the biocatalysis after appropriate working-up processes (cf. Example 1), and microparticles of poly(1,4-α-D-glucan). The results are shown in FIG. 6. One duplicate determination each was carried out, which again provides evidence of the high reproducibility of the results.

Example 14

Experiments on the Release from Theophylline Tablets Consisting of c) Microcrystalline Cellulose (Avicel™), d) Eudragit RS™ and e) Eudragit RL™ (Comparison Examples)

Figure 8:
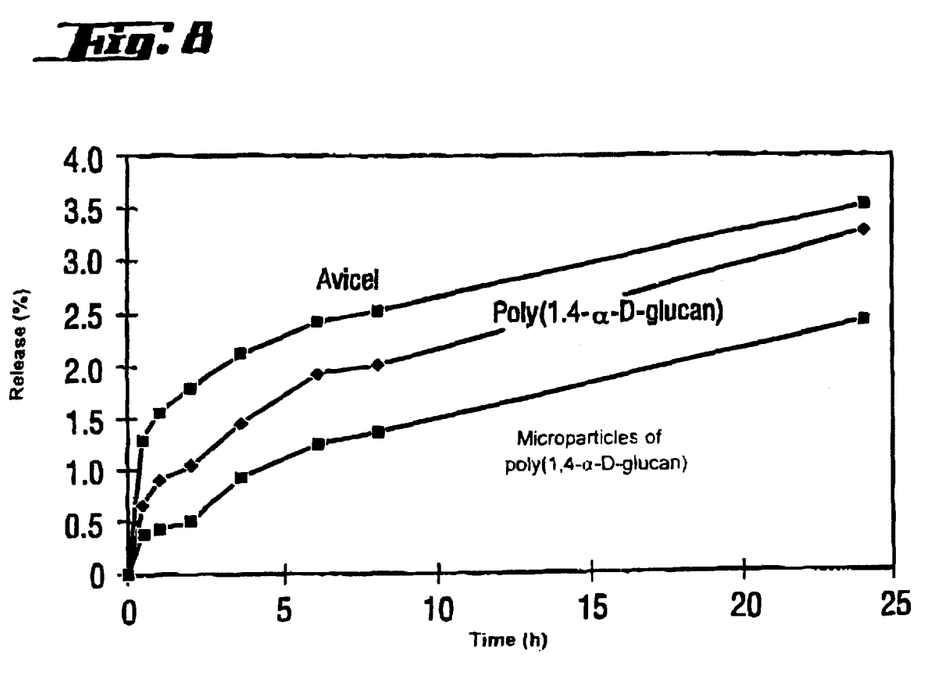
FIG. 8 is a plot showing the release of Ramorelix™ from tablets of various auxiliaries, according to Example 17.

The experiments on the release of theophylline from tablets of the comparison substance tablet auxiliaries are

TABLE 4

Concentration values of the aqueous supernatant as a function of time for the comparison substances microcrystalline cellulose (Avicel ™) and potato starch (Toffena ™)

| Tablet auxiliary | Release (hours) | | | | | | | | | | |
|---|---|---|---|---|---|---|---|---|---|---|---|
| | 0 | 0.5 | 1 | 2 | 3.5 | 6 | 8 | 10 | 24 | 32 | 48 |
| Microcrystalline cellulose (Avicel ™) | 0 | 6.99 | 13.38 | 34.31 | 52.40 | 65.53 | 75.12 | 77.13 | 78.36 | 72.80 | 79.75 |
| Microcrystalline cellulose (Avicel ™) | 0 | 6.51 | 14.84 | 22.30 | 31.53 | 43.89 | 52.40 | 67.23 | 84.70 | 81.92 | 84.39 |
| Microcrystalline cellulose (Avicel ™) | 0 | 4.81 | 17.68 | 26.12 | 37.51 | 50.54 | 57.50 | 57.50 | 95.05 | 100 | 100 |
| Potato starch (Toffena ™) | 0 | 7.99 | 74.65 | 77.28 | 76.51 | 78.98 | 78.98 | 78.98 | 83.15 | 80.53 | 84.08 |
| Potato starch (Toffena ™) | 0 | 12.18 | 33.54 | 39.57 | 65.07 | 69.86 | 77.43 | 84.08 | 87.48 | 85.32 | 82.07 |
| Potato starch (Toffena ™) | 0 | 93.97 | 74.34 | 77.28 | 81.14 | 84.70 | 80.53 | 80.53 | 87.79 | 87.48 | 87.48 |

FIG. 5:

The release of vitamin $B_{12}$ from tablets of various auxiliaries is shown in FIG. 5: a) poly(1,4-α-D-glycan), b) microparticles of poly(1,4-α-D-glucan), c) microcrystalline carried out analogously to Example 13. The tablet auxiliaries employed are: microcrystalline cellulose (Avicel™), Eudragit RS™ and Eudragit RL™. The results are shown in FIG. 8. One duplicate determination each was carried out.

In FIG. 6, the release profiles from Example 13 are juxtaposed comparatively.

FIG. 6 shows the release of theophylline from tablets of various auxiliaries: a) poly(1,4-α-D-glucan), b) microparticles of poly(1,4-α-D-glucan), c) microcrystalline cellulose (Avicel™), d) Eudragit RS™ and e) Eudragit RL™.

Example 15

Experiments on the Release from Theophylline Tablets Consisting of Poly(1,4-α-D-glucan), and also Microparticles of Poly(1,4-α-D-glucan) and Microcrystalline Cellulose (Avicel™) (Comparison Example) in Artificial Gastric Juice The experiments on the release of theophylline from tablets having the tablet auxiliaries poly(1,4α-D-glucan) (incl. microparticles) and microcrystalline cellulose (Avicel™) in artificial gastric juice were carried out analogously to Example 8 (artificial gastric juice: 2 g of sodium chloride, 3.2 g of pepsin, 7 ml of concentrated hydrochloric acid ($HCl_{aq}$), to be made up to one liter total volume with deionized water). Even when using a medium which reflects the natural environment the slow-release effects in the release can be observed reproducibly.

Figure 7:
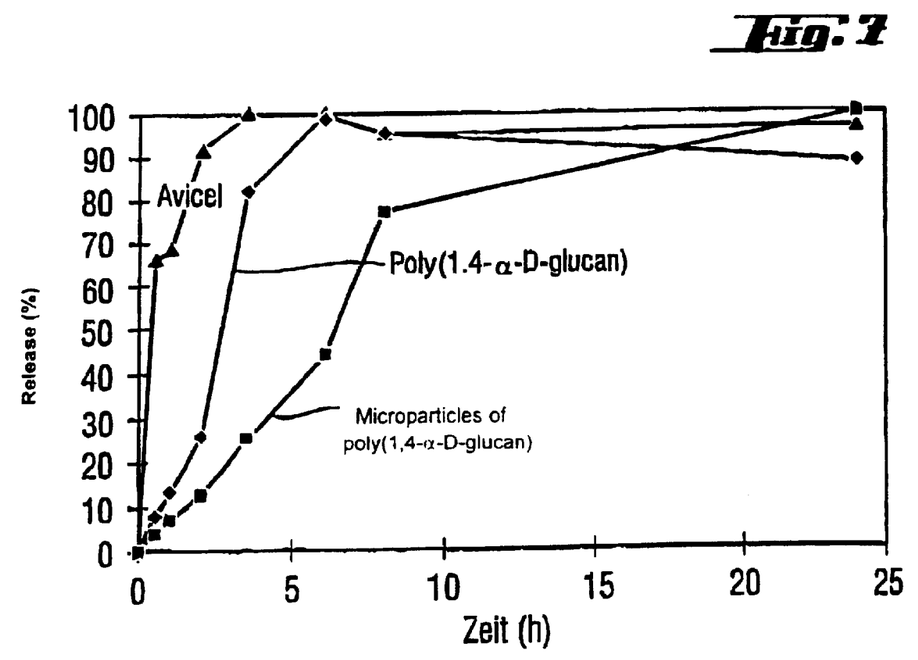
FIG. 7 is a plot showing the release of theophylline from tablets of various auxiliaries according to Example 15.

FIG. 7 shows the release of theophylline from tablets of various auxiliaries: a) poly(1,4-α-D-glucan), b) microparticles of poly(1,4-α-D-glucan) and c) microcrystalline cellulose (Avicel™) (comparison example).

Example 16

Experiments on the Release from Ramorelix Tablets Consisting of poly(1,4-α-D-glucan) and Microparticles Prepared Therefrom The experiments on the release from Ramorelix™ were carried out according to the previously described examples. Ramorelix™ is an LHRH antagonist having the following amino acid sequence (structure): 1-(N-acetyl-3-(2-naphthyl)-D-alanyl-p-chloro-D-phenylalanyl-D-tryptophyl-L-seryl-L-tyrosyl-0-(6-deoxy-alpha-L-mannopyranosyl)D-seryl-L-leucyl-L-arginyl-L-prolyl)semicarbazide acetate. The release medium employed, however, was artificial gastric juice instead of deionized water. The recipe for artificial gastric juice is: 2 g of sodium chloride, 3.2 g of pepsin, 7 ml of concentrated hydrochloric acid ($HCl_{aq}$) made up to one liter total volume with deionized water. The pH of the solution is 1.2.

Example 17

Experiment on the Release of Ramorelix Tablets Consisting of Microcrystalline Cellulose (Avicel™) (Comparison Example)

The experiments on the release are carried out as indicated in Example 8. The release medium used is artificial gastric juice.

FIG. 8 shows the release of Ramorelix™ from tablets of various auxiliaries: a) poly(1,4-α-D-glucan), b) microparticles of poly(1,4a-D-glucan) and c) microcrystalline cellulose (Avicel™) (comparison example).

Example 18

Determination of the Solubility of Polysaccharides 100 mg of poly(1,4-α-D-glucan) are added to 5 ml of double-distilled water. The reaction vessel is slowly heated with stirring (magnetic stirrer). It is heated in a step program with intervals of twenty degrees and observed with the eye. No changes are to be observed at temperatures of 40° C., 60° C., 80° C. and 100° C. According to these observations, the compound can be assigned the characteristic "water-insoluble".

Example 19

Determination of the Solubility of Polysaccharides and Classification According to the German Pharmacopeia (GP)

564 mg of poly(1,4-α-D-glucan) are heated in about 0.5 l of double-distilled water in an autoclave at 1.3 bar and 130° C. for 1.5 hours (Certoclav apparatus). The weight of the reaction vessel has been measured beforehand. The pressure in the apparatus is then released and it is cooled to room temperature. The contents are weighed. They correspond to 501.74 g. After a further 24 hours, the mixture is centrifuged and the supernatant is decanted. The solid residue is dried and weighed: 468 mg. A dissolved fraction of 96 mg is calculated therefrom. Based on the solvent employed, it is calculated therefrom that for 1 mg of poly(1,4-α-D-glucan) 5226 mg of water are necessary. According to the classification in the German Pharmacopeia, the classification results therefrom that this substance is "very poorly soluble", since between 1000 and 10,000 parts of solvent are necessary in order to bring 1 part of the substance into solution. Of the 7 classes for the classification of solubility (from "very readily soluble" (class 1) to "virtually insoluble" (class 7)), this is class number 6.

Example 20

Determination of the Solubility of Polysaccharides and Classification According to the German Pharmacopeia (GP)

The experiment is carried out as in Example 19. The only difference is a cooling process which is inserted after autoclave treatment and cooling to room temperature. The substance mixture is stored at 5° C. for 3 hours.

526 mg of poly(1,4-α-D-glucan) are weighed into about 480 ml of double-distilled water. After the heat treatment, a final weight of 468.09 g results. The dried sediment amounts to 488 mg. 38 mg of the poly(1,4-α-D-glucan) have therefore dissolved. This corresponds to a ratio of 1 mg of substance to 12,318 parts of solvent. The substance is therefore to be assigned to class number 7 as specified in the GP according to this treatment method and accordingly to be classified as virtually insoluble, because more than 10,000 parts of solvent are needed for one part of substance.

What is claimed is:

1. A slow-release tablet for controlled release of an active compound, said tablet comprising said active compound and at least one water-insoluble linear poly(1,4-α-D-glucan).

2. The slow-release tablet of claim 1 comprising at least one water-insoluble linear poly(1,4-α-D-glucan) prepared in a biotechnological process.

3. The slow-release tablet of claim 1 comprising at least one water-insoluble linear poly(1,4-α-D-glucan) prepared in a bidcatalytic process.

4. The slow-release tablet of claim 1 comprising at least one water-insoluble linear poly(1,4-α-D-glucan) prepared in a fermentation process.

5. The slow-release tablet of claim 1 wherein the water-insoluble linear poly(1,4-α-D-glucan) is present in the form of microparticles.

6. The slow-release tablet of claim 1 in biocompatible and/or pharmaceutically acceptable form.

7. The slow-release tablet of claim 1 further comprising at least one additive or auxiliary.

8. A method of administering an active compound to a patient, comprising the step of administering the slow-release tablet of claim 1 to a patient for controlled release of said active compound.

9. The method of claim 8, wherein said tablet is administered orally to said patient.

* * * * *